United States Patent [19]

Franko-Filipasic et al.

[11] 4,420,642
[45] Dec. 13, 1983

[54] SELECTIVE REMOVAL AND RECOVERY OF CATECHOL MIXED WITH 2-METHALLYLOXYPHENOL

[75] Inventors: Borivoj R. Franko-Filipasic, Morrisville, Pa.; James Snyder, Yardville, N.J.

[73] Assignee: FMC Corporation, Philadelphia, Pa.

[21] Appl. No.: 349,810

[22] Filed: Feb. 18, 1982

[51] Int. Cl.$^3$ .............................................. C07C 37/86
[52] U.S. Cl. ..................... 568/753; 568/652
[58] Field of Search ............................... 568/753, 652

[56] References Cited

U.S. PATENT DOCUMENTS 3,274,260  9/1966  Levy et al. .
3,927,118  12/1975 Ozretich .
4,250,333  2/1981  Rakoutz .

OTHER PUBLICATIONS

The Merck Index, 7th Ed., (1960), 879–880.
Chem. Abstracts, 70, 313, Abstract 87555b, (1969).

*Primary Examiner*—Bernard Helfin
*Attorney, Agent, or Firm*—Robert L. Andersen; H. Robinson Ertelt; Robert M. Kennedy

[57] ABSTRACT

A process is disclosed for selectively removing catechol from a mixture comprising catechol, 2-methallyloxyphenol, various salts, and by-products by treating the mixture with aqueous base, the aqueous phase being preferably saturated with respect to salts present; the catechol may then be recovered for recycle by acidifying the resulting aqueous phase and extracting the acidified aqueous phase with a suitable organic solvent.

7 Claims, No Drawings

SELECTIVE REMOVAL AND RECOVERY OF CATECHOL MIXED WITH 2-METHALLYLOXYPHENOL

The present invention relates to a process for preparation of 2-methallyloxyphenol from catechol and methallyl chloride. More particularly the invention relates to a process for selectively removing and recovering catechol from a mixture containing catechol, 2-methallyloxyphenol, and by-products of the reaction between catechol and methallyl chloride.

2-Methallyloxyphenol is an intermediate in the preparation of 2,3-dihydro-2,2-dimethyl-7-hydroxybenzofuran, the immediate precursor to the carbamate insecticide, carbofuran. It is well known in the art that 2-methallyloxyphenol may be prepared by reacting methallyl chloride and catechol. This reaction is known to produce as undesired by-products a diether, various ring alkylated by-products and salts such as sodium chloride. One method for minimizing the formation of the diether, 1,2-dimethallyloxybenzene, and also to minimize ring alkylation is to conduct the reaction between catechol and methallyl chloride so that it proceeds to only partial completion. This is readily accomplished by utilizing excess catechol. U.S. Pat. No. 3,927,118 describes such a process and points out the beneficial effects of not allowing the reaction to proceed to completion. While such a process does minimize formation of the diether and other undesired by-products, it also produces a reaction mixture containing substantial amounts of unreacted catechol. The present invention provides a simple and inexpensive process for the selective removal and recovery of unreacted catechol for reuse in the process. The method used to extract the unreacted catechol also dissolves the salts formed in the reaction and therefore eliminates a filtration step. The preferred embodiment also minimizes loss of solvent and provides an effluent substantially free of organic components.

The reaction of catechol and methallyl chloride may be illustrated as follows:

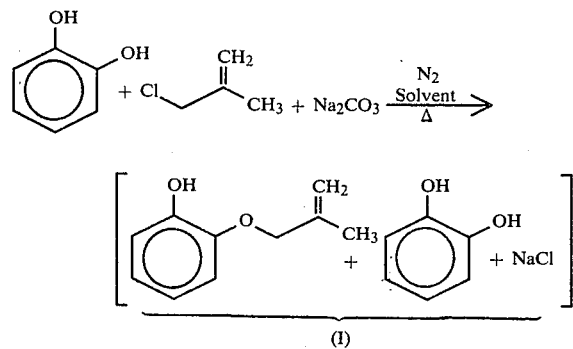

(I)

In accordance with existing processes the reaction mixture, I, would have been filtered to remove sodium chloride, then subjected to Claisen rearrangement and cyclization to form 2,3-dihydro-2,2-dimethyl-7-hydroxybenzofuran resulting in the loss of unreacted or excess catechol employed in the reaction.

In accordance with the present invention, catechol and reaction salts contained in the product mixture, I, are selectively removed and separated from 2-methallyloxyphenol by treating the product mixture with an aqueous solution of a strong base, preferably substantially saturated with a salt, then separating the resulting organic and aqueous phases. The catechol may be recovered by acidifying the aqueous phase then extracting catechol from the acidified aqueous phase with an organic solvent, preferably the solvent used in the reaction between catechol and methallyl chloride.

The starting material, I, for the present invention is a mixture resulting from the reaction of catechol and methallyl chloride containing unreacted catechol, methallyloxyphenol, salts of the reaction, an organic solvent, and by-products of the reaction. These by-products include, for example, from traces to substantial amounts of diether, 1,2-dimethallyloxybenzene, and various ring alkylated products, such as 3- 4-methallylcatechol or 3- or 4-isobutenylcatechol. The amount of diether and alkylated by-products present will depend on the conditions under which the reaction is run and the amount of reactants employed. High temperatures and long reaction times increase formation of such by-products, whereas formation of these by-products is minimized by using excess catechol. If excess catechol is employed, the excess is advantageously such that from about 40% to about 75%, most preferably 45-55% of the catechol used in the reaction is converted. This requires from about 1.3 to about 2.5 moles of catechol per mole of methallylchloride to be employed in the reaction.

In accordance with the process of this invention a mixture comprising unreacted catechol and 2-methallyloxyphenol is treated with an aqueous base capable of converting catechol to a corresponding dicatecholate, suitably by stirring, shaking, or other means of agitation, then separating resulting phases.

Bases suitable for use in the present invention are those which are water soluble and react with catechol to convert it to the dicatecholate, including alkali metal hydroxides, carbonates, or a mixture of them. Examples of such bases are sodium hydroxide, potassium hydroxide, sodium carbonate, potassium carbonate, or mixtures of them. At least two equivalents of base per mole of catechol should be employed to convert all catechol present to the corresponding dicatecholate, but a modest excess of base may be used if desired to assure complete conversion. Accordingly, one may employ from about 2 equivalents to about 3, preferably 2 to 2.5, equivalents of base per mole of catechol present in the reaction mixture. Thus, employing 1-1.5, preferably 1 to 1.25 moles of sodium or potassium carbonate or about 2 to 3, preferably 2 to 2.5, moles of sodium or potassium hydroxide will assure a high degree of selectivity for the separation of catechol from 2-methallyloxyphenol.

The amount of water employed in step 1 is preferably just sufficient to dissolve the catecholate formed and inorganic salts present in the mixture. That is, it is most preferable to use an aqueous solution of base the water content of which is such that, when mixed with the starting material, I, the aqueous phase will become saturated with catecholate and inorganic salts. It will immediately be apparent to one skilled in the art that if excess water is present, additional inorganic salts, e.g. sodium chloride, may be added to the reaction mixture or aqueous base solution to achieve a substantially saturated condition.

Limiting the amount of water, or adding additional salt, to produce a saturated solution of the dicatecholate and inorganic salts is particularly advantageous to reduce dissolution of organics other than the catecholate in the aqueous phase. This is particularly desirable where it is necessary to minimize uptake of partially water miscible solvents such as ketones, solvents normally employed in the preparation of 2-methallyloxyphenol, and when an aqueous effluent substantially free of organics is required. Achieving a substantially saturated condition also reduces emulsion formation, another source of losses of organics.

The extraction of catechol is most preferably carried out in the absence of oxygen, for example under an inert atmosphere such as a nitrogen or argon atmosphere. It has been found that air, more specifically oxygen, tends to cause some decomposition of the organic reactants causing the organic phase to turn dark. If air is executed during treatment with the aqueous base this degradation does not occur.

The phases may be separated in any desired manner. The organic phase, containing 2-methallyloxyphenol and/or the corresponding salt thereof, depleted of catechol, is then washed with aqueous acid, for example aqueous hydrochloric, most preferably saturated with a salt, such as sodium or potassium chloride, to provide 2-methallyloxyphenol for rearrangement and cyclization to 2,3-dihydro-2,2-dimethyl-7-hydroxybenzofuran. The aqueous phase from the acid wash of the organic phase may be recycled one or more times as required for further treatment with aqueous base. The aqueous phase resulting from the treatment with aqueous base, containing the catecholate and inorganic salts is acidified with an aqueous solution of a water soluble acid, for example hydrochloric acid, most preferably saturated with a salt such as sodium or potassium chloride, to convert the catecholate to catechol. During this wash at least two equivalents of acid should be employed per mole of catecholate, and preferably excess acid is employed. While hydrochloric acid is preferred many other acids may also be employed in this step, for example, nitric, sulfuric, etc., as will be apparent to those skilled in the art.

The catechol is separated from the water soluble salts by extracting the acidified aqueous solution with an organic solvent. Solvents of choice are those which may be employed for the reaction of catechol with methallyl chloride, permitting the catechol/solvent mixture to be recycled directly for conversion to 2-methallyloxyphenol. Solvents of choice for this purpose are ketones, preferably alkyl ketones such as diisobutyl ketone, or methyl isobutyl ketone.

Other solvents capable of extracting catechol from water may, however, be employed without departing from the spirit and scope of the invention. Thus one may employ various petroleum distillates such as Soltrol ® 50, a hydrocarbon distillate, or an aromatic or aliphatic hydrocarbon such as benzene, toluene, n-hexane or n-heptane, or mixtures thereof. It will be apparent that if the solvent is not suitable for use in the reaction of catechol and methallyl chloride, that the solvent used for extraction may be evaporated and a second solvent used in the reaction.

In the preferred embodiment, following the organic extraction of catechol from the acidified aqueous phase, the remaining aqueous phase, containing inorganic salts and substantially free of organics, may be discarded.

The following example illustrates the practice of the present invention.

EXAMPLE 1

Under a dry nitrogen atmosphere a stirred mixture of 220.0 grams (2.0 moles) of catechol, 63.6 grams (0.6 mole) of sodium carbonate and 1.8 grams (0.01 mole) of potassium iodide in 975 grams of methyl isobutyl ketone (MIBK) was heated at reflux. While at reflux 100.0 grams (1.1 moles) of methallyl chloride were added dropwise during a four hour period. The reaction mixture was stirred at reflux for one hour. Azeotroped water was collected in a Dean-Stark trap throughout the reaction. The mixture was then allowed to cool.

A solution containing 85.0 grams of sodium hydroxide in 400.0 grams of ice water (sparged with nitrogen) was added to the reaction mixture. The total was stirred vigorously under a nitrogen atmosphere for one hour during which the precipitated salts dissolved in the aqueous phase. The stirring was stopped and the mixture separated into two phases with a slight emulsion in between. Water, 25.0 ml, was added to aid in breaking the emulsion. The aqueous phase (1) was separated from the organic phase (2) and extracted with two 250 ml portions of MIBK. The MIBK extractions were combined with the organic phase (2). Gas chromatographic analysis of the combined organic phase (2) indicated that it contained over 15 grams of catechol.

The aqueous phase (1) was acidified to a pH of about 2 with a dilute, 18%, aqueous hydrogen chloride solution. The acidified aqueous solution was extracted with one 500 ml and two 250 ml portions of MIBK. The remaining acidified aqueous phase (3) was saved. The organic extracts were combined and the solvent evaporated under reduced pressure to yield a liquid which contained crystalline catechol. The solid was filtered to give 90.5 grams of catechol. The filtrate contained 5.3 grams of 2-methallyloxyphenol. The organic phase (2) was added to the acidified aqueous phase (3) and the mixture retreated with 40 grams of a 25% aqueous sodium hydroxide solution, shaken vigorously and allowed to separate into two phases. The aqueous phase (4) was separated from the organic phase (5) and acidified with a dilute, 18%, aqueous hydrogen chloride solution. The acidified solution was extracted with MIBK. The extracts were combined and evaporated under reduced pressure to leave a liquid. Gas chromatographic analysis of this liquid indicated 16.3 grams of catechol and 3.9 grams of 2-methallyloxyphenol. The organic phase (5) was washed with dilute aqueous hydrogen chloride then concentrated under reduced pressure to 180.7 grams. Gas chromatographic analysis indicated 129.2 grams of 2-methallyloxyphenol and 3.9 grams of catechol.

EXAMPLE II

Under a dry nitrogen atmosphere a stirred mixture of 55.0 grams (0.5 mole) of catechol, 26.5 grams (0.25 mole) of sodium carbonate and 0.83 gram (0.005 mole) of potassium iodide in 220.0 grams of methyl isobutyl ketone (MIBK) was heated to reflux. While at reflux 27.2 grams (0.3 mole) of methallyl chloride were added dropwise during a 1.5 hour period. After complete addition the reaction mixture was stirred at reflux for 3.25 hours. Azeotroped water was collected in a Dean-Stark trap throughout the reaction. The mixture was cooled and 125.0 grams of an aqueous 10.5% sodium hydroxide solution (saturated with sodium chloride and sparged with nitrogen) was added. An additional 100.0 grams of nitrogen sparged water was added to the mixture to dissolve the reaction salts. The total was stirred vigorously under a nitrogen atmosphere for 10 minutes. The stirring was stopped and the mixture separated into an aqueous phase (1) and an organic phase (2). While under a nitrogen atmosphere, the aqueous phase (1) was added to 58.5 grams of cold concentrated hydrochloric acid and the resulting mixture (3) stirred vigorously. Also under a nitrogen atmosphere, the organic phase (2) was washed with 50.0 ml of a 5.5% aqueous hydrochloric acid solution (saturated with sodium chloride and degassed as above). The acidic aqueous wash was added to (3). The washed organic phase (2) was analyzed by gas chromatography and found to contain 30.1 grams of 2-methallyloxyphenol, 3.1 grams of catechol, and a trace of by-products. The acidified aqueous phase (3) was extracted with 150.0 grams of MIBK. The extract was analyzed by gas chromatography and found to contain 27.0 grams of catechol, 0.8 grams of 2-methallyloxyphenol, and 0.1 gram of by-products.

We claim:

1. A process for selectively removing unreacted catechol from a mixture comprising catechol, 2-methallyloxyphenol, reaction salts, and an organic solvent comprising treating said mixture with an aqueous solution of a base selected from an alkali metal hydroxide or carbonate, the aqueous solution comprising from 2 to 2.5 equivalents of base per mole of catechol present in said mixture, separating the resulting aqueous phase from the resulting organic phase, then recovering catechol from the aqueous phase.

2. The process of claim 1 in which the water content of said aqueous base is such that, upon treatment of said reaction mixture, the resulting aqueous phase becomes substantially saturated with salts present prior to treatment of the reaction mixture and those formed upon treatment with said base.

3. The process of claim 2 in which said treatment is conducted in an inert atmosphere substantially free of oxygen.

4. The process of claim 1 in which said treatment is conducted in an inert atmosphere substantially free of oxygen.

5. The process of claim 4 in which said treatment is conducted under an atmosphere comprising an inert gas selected from nitrogen or argon.

6. The process of claim 1, 2, 4 or 3 including the additional steps comprising
   (a) acidifying the resulting aqueous phase with an aqueous acid, at least two equivalents of acid per mole of catecholate present in the aqueous phase being utilized; then
   (b) treating the acidified aqueous phase with sufficient organic solvent to extract the catechol present.

7. The process of claim 6 in which the organic solvent for step (b) is the solvent employed for reaction of catechol with methallyl chloride to prepare the starting reaction mixture.

* * * * *

UNITED STATES PATENT AND TRADEMARK OFFICE
CERTIFICATE OF CORRECTION

PATENT NO. : 4,420,642
DATED : December 13, 1983
INVENTOR(S) : Borivoj R. Franko-Filipasic; James Snyder It is certified that error appears in the above—identified patent and that said Letters Patent is hereby corrected as shown below:

On the title page,

Title, "Selective Removal and Recovery of Catechol Mixed with 2-Methallyloxyphenol" should read --Selective Removal and Recovery of Catechol from a 2-Methallyloxyphenol/Catechol Mixture--.

Signed and Sealed this

Twelfth Day of March 1985

[SEAL]

Attest:

DONALD J. QUIGG

*Attesting Officer*   Acting Commissioner of Patents and Trademarks